United States Patent
Huston Davenport et al.

(10) Patent No.: US 10,266,864 B2
(45) Date of Patent: Apr. 23, 2019

(54) ENZYMES HAVING PULLULANASE ACTIVITY

(71) Applicant: BASF ENZYMES LLC, San Diego, CA (US)

(72) Inventors: Adrienne Huston Davenport, San Diego, CA (US); Hugo D. Urbina, San Diego, CA (US); Kenneth E. Barrett, San Diego, CA (US); Danielle Cusumano, San Diego, CA (US)

(73) Assignee: BASF Enzymes LLC, San Diego, CA (US)

( * ) Notice: Subject to any disclaimer, the term of this patent is extended or adjusted under 35 U.S.C. 154(b) by 0 days.

(21) Appl. No.: 14/773,696

(22) PCT Filed: Mar. 10, 2014

(86) PCT No.: PCT/US2014/022542
§ 371 (c)(1),
(2) Date: Sep. 8, 2015

(87) PCT Pub. No.: WO2014/150195
PCT Pub. Date: Sep. 25, 2014

(65) Prior Publication Data
US 2016/0046971 A1    Feb. 18, 2016

Related U.S. Application Data

(60) Provisional application No. 61/801,084, filed on Mar. 15, 2013.

(51) Int. Cl.
  *C12P 19/16*     (2006.01)
  *C12P 19/02*     (2006.01)
  *C12N 9/44*      (2006.01)

(52) U.S. Cl.
  CPC ............ *C12P 19/16* (2013.01); *C12N 9/2451* (2013.01); *C12N 9/2457* (2013.01); *C12P 19/02* (2013.01);
  (Continued)

(58) Field of Classification Search
  None
  See application file for complete search history.

(56) References Cited

U.S. PATENT DOCUMENTS 5,055,403 A * 10/1991 Tomimura ........... C12N 9/2457
                                              435/100
5,312,739 A *  5/1994 Shaw ..................... C12P 19/14
                                              435/100
5,721,127 A *  2/1998 Deweer ................ C12N 9/2451
                                              435/210

(Continued)

FOREIGN PATENT DOCUMENTS

WO    WO 9202614 A1 *  2/1992  ........... C12N 9/2457

OTHER PUBLICATIONS

GenBank Accession No. ADH63307.1, published May 16, 2011.*

(Continued)

*Primary Examiner* — Richard C Ekstrom
(74) *Attorney, Agent, or Firm* — Richa Dhindsa (57) ABSTRACT

The present invention relates to thermostable pullulanases useful for industrial and scientific purposes. The present invention provides methods for producing the modified pullulanase, enzymatic compositions comprising the modified pullulanase, and methods for use of the enzymatic compositions.

18 Claims, 5 Drawing Sheets
Specification includes a Sequence Listing.

(52) U.S. Cl.
CPC ....... *C12Y 302/01041* (2013.01); *Y02E 50/17* (2013.01)

(56) References Cited

U.S. PATENT DOCUMENTS

| | | | |
|---|---|---|---|
| 6,043,074 A | 3/2000 | Duffner | |
| 6,284,498 B1* | 9/2001 | Fouache | C12P 19/22 435/100 |
| 2002/0081670 A1* | 6/2002 | Bisgard-Frantzen | C12N 9/2451 435/101 |
| 2006/0211087 A1* | 9/2006 | Roosild | C07K 14/32 435/69.1 |
| 2015/0037844 A1* | 2/2015 | Lee | C12P 19/02 435/96 |

OTHER PUBLICATIONS

Guo et al., "Protein tolerance to random amino acid change", Proceedings of the National Academy of Sciences USA, vol. 101, No. 25, pp. 9205-9210, 2004.*
PCT/US2014/022542—Written Opinion—(dated Aug. 5, 2014).
HII—Enzyme Res. Hindawi Publishing Corp. (2012)—2012:921362—14 pages.
NCBI Reference Sequence No. YP_003684815—Sikorski—Meiothermus silvanus DSM 9946 (2012).
GenBank Accession No. CP002042.1—Meiothermus silvanus DSM 9946 (2011).
UniProt Accession No. D7BEV4—Alpha amylase catalytic region (2008).
UniProt Accession No. E8PPY0—Pullulan hydrolase type III (2011).
EP 14 76 7656—EP Extended Search Report (dated Aug. 9, 2016).

* cited by examiner

SEQ ID No. 1, Pullulanase, DNA

ATGACCGCCCAACGACCCCCGCCCACCGGCCCGATTCCGGTCGTCGGCCCCACCCGGCCCCAACCCAGCGGCGAC
CTCAACTTCGAGCACGACCCCAAGCTGCCCAAATTCGTCTCGCTGGCGGCGGATGGGCTCTCGGTGCGCTTTCAGG
CCGGGGAGGGCTCGGTGAAGTGGGCCATCGTCCAGGCCGAGGGCAGGAACTACCCCATGCACCGGCAGCTCTGG
CAGGACGGCAGCGAGATCTGGCGGGTAGCGCTTCCCCCCAGCATAAAGAACTACCGCATCCGCCTCGAGACCGCC
CAGAATAAGCCCGCCGTGTTCGGCCCTTTTGACGCGAATCATCCGTTGGTGGGCCTGGACTGGGTAGGGAAGAGC
ATCGGCTACCAGGTCTTCCCCGAACGCTTCTGGAATGGGGACAAAACCAACGACATGCGGGCGCTCGAGACCGAC
GAGTACCGCTTCAACGAGACCTGGAACCAGAACCCCCAGGCGACTAAGCCCTACCTATCGAACTGGAACGACCCA
CCCGGTGAGCTGCACTGCTGCCACCAGTATTTCGGTGGCGACCTAGCCGGGTTCCTGGAGAAGCTCCCCCACCTCG
AGGCTTTGGGGGTCAGGCTCGTCTACTTCAACCCGCTCTTCGACTCCGGCTCCGCCCACGGCTACGACACCCACGA
CTACTACAAAATCTCTCCCAAATTCGGCGACGAGGCTCTTCTACGGCAGGTGCTGGACGCAGCCCACGCCCAGGG
GATGCGGGTGATCTTCGACTTCGTACCCAACCACACTGGCCTGGGCTTCTTCGCCTTCCAGGACGTGGTGAAAAAC
GGGCGGGCCTCCCAGTACTGGAACTGGTACACGATTAGGCGATGGCCGTTCCGTCCCGGCGACGCCTCGGCCTAC
GACACCTTCTCGGGGGTGGGGAGCTTACCCAAGCTCAACACCGCCAACCCCGAGGTGAAAAAGTATCTGCTCGAG
GTGGCCGAGCACTGGATGCGCTTCGGCTTCGACGGTTTGCGCGTCGACTACCCACAGGGCATCGTGAACCGCGAG
GATTTCTACCGCGACCTGCGCCGGGTGGTGAAGGGGGTTAAACCCGATGCCTACATCGTGGCCGAGATCTGGGCG
CGGGACCCCAGCTGGCTGCAAGGCGACCAGGCCGATAGCCTGATGAACTACGCCATCGGGCGGGACATTGTGCT
GCGCTTCGCCCGGGGCGGCGGGGTGGCTTTGTACAGTGGACGGCGGGCCTTGGCCGATCTAGTCCGCATCTACAC
CGATTACCCCGAGGCGGTGGTGGGCCAGGGGTGGAACCTCATTGGCTCACACGATACTCCCAGGGTGCTCACCGA
TTTGGGTGGGGGTGCTCTAGGCGACACCCCGTCGCCCGAGTCGCTGGCCCGACTGCGCCTGGCCATGGGCTTGCT
CTACGCCCTCCCCGGAATGCCGATTTTCTTCCAGGGGGATGAGTGCGGTTTCACCGGGGAGGCCGGGCAGTACCC
GGTCAATGAGCTATACCGCTACCCAATCCAGTGGGACCGGTGCAACCCCGACGTGCTGGAGTTTTACCAGCGACT
CGGCAAGGTTCGGGCTGGCCTAGCCGCTCTGCAAGGCCCGGCGTTCCGGGCCTACGCGGGTGAGGGGGCGGTGT
TGGCTTTTCTGCGGGGCGAGCCAGGTCAGGAGGTGGTGTTGGCGGCTTTCAACAAGGGCAGCGAACCAGCCAAC
CTGGCCCTTCCCGGCGGCACCTGGCGCGATGCCCTTAGCGGCCAGACCTTCCAAAGCCAAGCAGAACTCCCGGCG
ATTGGTTTTCGCTATCTCGTACGGGCTGGGCAGTAG

FIGURE 4

SEQ ID No. 2, Pullulanase, Polypeptide

MTAQRPPPTGPIPVVGPTRPQPSGDLNFEHDPKLPKFVSLAADGLSVRFQAGEGSVKWAIVQAEGRNYPMHRQLWQ
DGSEIWRVALPPSIKNYRIRLETAQNKPAVFGPFDANHPLVGLDWVGKSIGYQVFPERFWNGDKTNDMRALETDEYRF
NETWNQNPQATKPYLSNWNDPPGELHCCHQYFGGDLAGFLEKLPHLEALGVRLVYFNPLFDSGSAHGYDTHDYYKIS
PKFGDEALLRQVLDAAHAQGMRVIFDFVPNHTGLGFFAFQDVVKNGRASQYWNWYTIRRWPFRPGDASAYDTFSG
VGSLPKLNTANPEVKKYLLEVAEHWMRFGFDGLRVDYPQGIVNREDFYRDLRRVVKGVKPDAYIVAEIWARDPSWLQ
GDQADSLMNYAIGRDIVLRFARGGGVALYSGRRALADLVRIYTDYPEAVVGQGWNLIGSHDTPRVLTDLGGGALGDTP
SPESLARLRLAMGLLYALPGMPIFFQGDECGFTGEAGQYPVNELYRYPIQWDRCNPDVLEFYQRLGKVRAGLAALQGP
AFRAYAGEGAVLAFLRGEPGQEVVLAAFNKGSEPANLALPGGTWRDALSGQTFQSQAELPAIGFRYLVRAGQ*

FIGURE 5

SEQUENCE LISTING

<160> NUMBER OF SEQ ID NOS: 2

<210> SEQ ID NO 1
<211> LENGTH: 1836
<212> TYPE: DNA
<213> ORGANISM: Thermococcus celer

<400> SEQUENCE: 1

```
atgaccgccc aacgacccccc gcccaccggc ccgattccgg tcgtcggccc caccoggccc     60
caacccagcg gcgacctcaa cttcgagcac gaccccaagc tgcccaaatt cgtctcgctg    120
gcggcggatg ggctctcggt gcgctttcag gccggggagg gctcggtgaa gtgggccatc    180
gtccaggccg agggcaggaa ctaccccatg caccggcagc tctggcagga cggcagcgag    240
atctggcggg tagcgcttcc ccccagcata aagaactacc gcatccgcct cgagaccgcc    300
cagaataagc ccgccgtgtt cggcccttt gacgcgaatc atccgttggt gggcctggac    360
tgggtaggga agagcatcgg ctaccaggtc ttcccccgaac gcttctggaa tggggacaaa    420
accaacgaca tgcgggcgct cgagaccgac gagtaccgct tcaacgagac ctggaaccag    480
aaccccccagg cgactaagcc ctacctatcg aactggaacg acccaccgg tgagctgcac    540
tgctgccacc agtatttcgg tggcgaccta gccgggttcc tggagaagct ccccccacctc    600
gaggctttgg gggtcaggct cgtctacttc aacccgctct tcgactccgg ctccgcccac    660
ggctacgaca cccacgacta ctacaaaatc tctcccaaat tcggcgacga ggctcttcta    720
cggcaggtgc tggacgcagc ccacgcccag gggatgcggg tgatcttcga cttcgtaccc    780
aaccacactg gcctgggctt cttcgccttc caggacgtgg tgaaaaacgg gcgggcctcc    840
cagtactgga actggtacac gattaggcga tggccgttcc gtcccggcga cgcctcggcc    900
tacgacacct tctcggggt ggggagctta cccaagctca acaccgccaa ccccgaggtg    960
aaaaagtatc tgctcgaggt ggccgagcac tggatgcgct tcggcttcga cggtttgcgc   1020
gtcgactacc cacagggcat cgtgaaccgc gaggatttct accgcgacct cgccgggtg    1080
gtgaaggggg ttaaacccga tgcctacatc gtggccgaga tctgggcgcg ggaccccagc   1140
tggctgcaag cgaccaggc cgatagcctg atgaactacg ccatcgggcg ggacattgtg   1200
ctgcgcttcg cccggggcgg cggggtggct ttgtacagtg gacggcgggc cttggccgat   1260
ctagtccgca tctacaccga ttaccccgag gcggtggtgg gccaggggtg gaacctcatt   1320
ggctcacacg atactcccag ggtgctcacc gatttgggtg ggggtgctct aggcgacacc   1380
ccgtcgcccg agtcgctggc ccgactgcgc ctggccatgg gcttgctcta cgccctcccc   1440
ggaatgccga ttttcttcca ggggatgag tgcggtttca ccggggaggc cgggcagtac   1500
ccggtcaatg agctataccg ctacccaatc cagtgggacc ggtgcaaccc cgacgtgctg   1560
gagtttacc agcgactcgg caaggttcgg gctggcctag ccgctctgca aggcccggcg    1620
ttccgggcct acgcgggtga gggggcggtg ttggcttttc tgcggggcga gccaggtcag   1680
gaggtggtgt tggcggcttt caacaagggc agcgaaccag ccaacctggc ccttcccggc   1740
ggcacctggc gcgatgccct tagcggccag accttccaaa gccaagcaga actcccggcg   1800
attggttttc gctatctcgt acgggctggg cagtag                              1836
```

<210> SEQ ID NO 2

```
<211> LENGTH: 611
<212> TYPE: PRT
<213> ORGANISM: Thermococcus celer

<400> SEQUENCE: 2
```

| | | | | | | | | | | | | | | |
|---|---|---|---|---|---|---|---|---|---|---|---|---|---|---|
| Met | Thr | Ala | Gln | Arg | Pro | Pro | Thr | Gly | Pro | Ile | Pro | Val | Val | Gly |
| 1 | | | | 5 | | | | | 10 | | | | | 15 |
| Pro | Thr | Arg | Pro | Gln | Pro | Ser | Gly | Asp | Leu | Asn | Phe | Glu | His | Asp | Pro |
| | | | 20 | | | | | 25 | | | | | 30 | |
| Lys | Leu | Pro | Lys | Phe | Val | Ser | Leu | Ala | Ala | Asp | Gly | Leu | Ser | Val | Arg |
| | | 35 | | | | | 40 | | | | | 45 | | |
| Phe | Gln | Ala | Gly | Glu | Gly | Ser | Val | Lys | Trp | Ala | Ile | Val | Gln | Ala | Glu |
| 50 | | | | | 55 | | | | | 60 | | | | | |
| Gly | Arg | Asn | Tyr | Pro | Met | His | Arg | Gln | Leu | Trp | Gln | Asp | Gly | Ser | Glu |
| 65 | | | | | 70 | | | | | 75 | | | | | 80 |
| Ile | Trp | Arg | Val | Ala | Leu | Pro | Pro | Ser | Ile | Lys | Asn | Tyr | Arg | Ile | Arg |
| | | | | 85 | | | | | 90 | | | | | 95 | |
| Leu | Glu | Thr | Ala | Gln | Asn | Lys | Pro | Ala | Val | Phe | Gly | Pro | Phe | Asp | Ala |
| | | | 100 | | | | | 105 | | | | | 110 | | |
| Asn | His | Pro | Leu | Val | Gly | Leu | Asp | Trp | Val | Gly | Lys | Ser | Ile | Gly | Tyr |
| | | 115 | | | | | 120 | | | | | 125 | | | |
| Gln | Val | Phe | Pro | Glu | Arg | Phe | Trp | Asn | Gly | Asp | Lys | Thr | Asn | Asp | Met |
| 130 | | | | | 135 | | | | | 140 | | | | | |
| Arg | Ala | Leu | Glu | Thr | Asp | Glu | Tyr | Arg | Phe | Asn | Glu | Thr | Trp | Asn | Gln |
| 145 | | | | | 150 | | | | | 155 | | | | | 160 |
| Asn | Pro | Gln | Ala | Thr | Lys | Pro | Tyr | Leu | Ser | Asn | Trp | Asn | Asp | Pro | Pro |
| | | | | 165 | | | | | 170 | | | | | 175 | |
| Gly | Glu | Leu | His | Cys | Cys | His | Gln | Tyr | Phe | Gly | Gly | Asp | Leu | Ala | Gly |
| | | | 180 | | | | | 185 | | | | | 190 | | |
| Phe | Leu | Glu | Lys | Leu | Pro | His | Leu | Glu | Ala | Leu | Gly | Val | Arg | Leu | Val |
| | | 195 | | | | | 200 | | | | | 205 | | | |
| Tyr | Phe | Asn | Pro | Leu | Phe | Asp | Ser | Gly | Ser | Ala | His | Gly | Tyr | Asp | Thr |
| 210 | | | | | 215 | | | | | 220 | | | | | |
| His | Asp | Tyr | Tyr | Lys | Ile | Ser | Pro | Lys | Phe | Gly | Asp | Glu | Ala | Leu | Leu |
| 225 | | | | | 230 | | | | | 235 | | | | | 240 |
| Arg | Gln | Val | Leu | Asp | Ala | Ala | His | Ala | Gln | Gly | Met | Arg | Val | Ile | Phe |
| | | | | 245 | | | | | 250 | | | | | 255 | |
| Asp | Phe | Val | Pro | Asn | His | Thr | Gly | Leu | Gly | Phe | Phe | Ala | Phe | Gln | Asp |
| | | | | 260 | | | | | 265 | | | | | 270 | |
| Val | Val | Lys | Asn | Gly | Arg | Ala | Ser | Gln | Tyr | Trp | Asn | Trp | Tyr | Thr | Ile |
| | | 275 | | | | | 280 | | | | | 285 | | | |
| Arg | Arg | Trp | Pro | Phe | Arg | Pro | Gly | Asp | Ala | Ser | Ala | Tyr | Asp | Thr | Phe |
| 290 | | | | | 295 | | | | | 300 | | | | | |
| Ser | Gly | Val | Gly | Ser | Leu | Pro | Lys | Leu | Asn | Thr | Ala | Asn | Pro | Glu | Val |
| 305 | | | | | 310 | | | | | 315 | | | | | 320 |
| Lys | Lys | Tyr | Leu | Leu | Glu | Val | Ala | Glu | His | Trp | Met | Arg | Phe | Gly | Phe |
| | | | | 325 | | | | | 330 | | | | | 335 | |
| Asp | Gly | Leu | Arg | Val | Asp | Tyr | Pro | Gln | Gly | Ile | Val | Asn | Arg | Glu | Asp |
| | | | 340 | | | | | 345 | | | | | 350 | | |
| Phe | Tyr | Arg | Asp | Leu | Arg | Arg | Val | Lys | Gly | Val | Lys | Pro | Asp | Ala |
| | | 355 | | | | | 360 | | | | | 365 | | | |
| Tyr | Ile | Val | Ala | Glu | Ile | Trp | Ala | Arg | Asp | Pro | Ser | Trp | Leu | Gln | Gly |
| | | 370 | | | | | 375 | | | | | 380 | | | |
| Asp | Gln | Ala | Asp | Ser | Leu | Met | Asn | Tyr | Ala | Ile | Gly | Arg | Asp | Ile | Val |

-continued

```
385                 390                 395                 400
Leu Arg Phe Ala Arg Gly Gly Val Ala Leu Tyr Ser Gly Arg Arg
            405                 410                 415

Ala Leu Ala Asp Leu Val Arg Ile Tyr Thr Asp Tyr Pro Glu Ala Val
            420                 425                 430

Val Gly Gln Gly Trp Asn Leu Ile Gly Ser His Asp Thr Pro Arg Val
            435                 440                 445

Leu Thr Asp Leu Gly Gly Ala Leu Gly Asp Thr Pro Ser Pro Glu
    450                 455                 460

Ser Leu Ala Arg Leu Arg Leu Ala Met Gly Leu Leu Tyr Ala Leu Pro
465             470                 475                 480

Gly Met Pro Ile Phe Phe Gln Gly Asp Glu Cys Gly Phe Thr Gly Glu
                485                 490                 495

Ala Gly Gln Tyr Pro Val Asn Glu Leu Tyr Arg Tyr Pro Ile Gln Trp
            500                 505                 510

Asp Arg Cys Asn Pro Asp Val Leu Glu Phe Tyr Gln Arg Leu Gly Lys
            515                 520                 525

Val Arg Ala Gly Leu Ala Ala Leu Gln Gly Pro Ala Phe Arg Ala Tyr
    530                 535                 540

Ala Gly Glu Gly Ala Val Leu Ala Phe Leu Arg Gly Glu Pro Gly Gln
545                 550                 555                 560

Glu Val Val Leu Ala Ala Phe Asn Lys Gly Ser Glu Pro Ala Asn Leu
                565                 570                 575

Ala Leu Pro Gly Gly Thr Trp Arg Asp Ala Leu Ser Gly Gln Thr Phe
            580                 585                 590

Gln Ser Gln Ala Glu Leu Pro Ala Ile Gly Phe Arg Tyr Leu Val Arg
        595                 600                 605

Ala Gly Gln
610
```

ENZYMES HAVING PULLULANASE ACTIVITY

FIELD OF THE INVENTION

This invention relates generally to enzymes, polynucleotides encoding the enzymes, the use of such polynucleotides and polypeptides, and more specifically to enzymes having pullulanase activity.

SEQUENCE LISTING

This application is being filed electronically via the USPTO EFS-WEB server, as authorized and set forth in MPEP § 502.05 and this electronic filing includes an electronically submitted sequence listing; the entire content of this sequence listing is hereby incorporated by reference into the specification of this application. The sequence listing is identified on the electronically filed ASCII (.txt) text file as follows:

| File Name | Date of Creation | Size |
|---|---|---|
| SEQLIST_D2580 | 7 Mar. 2014 | 7,960 bytes |

BACKGROUND

Pullulanase is a specific kind of glucanase, an amylolytic exoenzyme, that degrades pullulan. Type I pullulanases specifically attack alpha-1,6 linkages, while type II pullulanases are also able to hydrolyse alpha-1,4 linkages.

Pullulanase (EC 3.2.1.41) is also known as pullulan-6-glucanohydrolase (Debranching enzyme). Its substrate, pullulan, is regarded as a chain of maltotriose units linked by alpha-1,6-glycosidic bonds. Pullulanase will hydrolytically cleave pullulan (alpha-glucan polysaccharides).

Pullulanases are used for several industrial and commercial applications, including, saccharification of starch, liquefaction of starch, production of high-maltose corn syrup, production of high-fructose corn syrup, starch processing, in detergents, production of cyclodextrins, and production of low-calorie beer, in the baking industry, as well as dental plaque control. (Siew Ling Hii, Joo Shun Tan, Tau Chuan Ling, and Arbakariya Bin Ariff, "Pullulanase: Role in Starch Hydrolysis and Potential Industrial Applications," Enzyme Research, vol. 2012, Article ID 921362, 14 pages, 2012.)

SUMMARY OF THE INVENTION

The invention provides an isolated nucleic acid having a sequence as set forth in SEQ ID No.: 1 and variants thereof having at least 50% sequence identity to SEQ ID No.: 1 and encoding polypeptides having pullulanase activity, or encoding polypeptides having pullulanase activity having at least 50% sequence identity to SEQ ID No.: 2.

One aspect of the invention is an isolated nucleic acid having a sequence as set forth in SEQ ID No.: 1, sequences substantially identical thereto, and sequences complementary thereto.

Another aspect of the invention is an isolated nucleic acid including at least 10 consecutive bases of a sequence as set forth in SEQ ID No: 1 nucleic acid sequences, sequences substantially identical thereto, and the sequences complementary thereto.

In yet another aspect, the invention provides an isolated nucleic acid encoding a polypeptide having a sequence as set forth in SEQ ID No.: 2 and variants thereof encoding a polypeptide having pullulanase activity and having at least 50% sequence identity to such sequences. Another aspect of the invention is an isolated nucleic acid encoding a polypeptide or a functional fragment thereof having a sequence as set forth in SEQ ID No.: 2, and sequences substantially identical thereto.

Another aspect of the invention is an isolated nucleic acid encoding a polypeptide having at least 10 consecutive amino acids of a sequence as set forth in SEQ ID No.: 2, and sequences substantially identical thereto.

In yet another aspect, the invention provides a purified polypeptide having a sequence as set forth in SEQ ID No.: 2, and sequences substantially identical thereto Another aspect of the invention is a method of making a polypeptide having a sequence as set forth in SEQ ID No.: 2, and sequences substantially identical thereto. The method includes introducing a nucleic acid encoding the polypeptide into a host cell, wherein the nucleic acid is operably linked to a promoter, and culturing the host cell under conditions that allow expression of the nucleic acid.

Another aspect of the invention is a method of making a polypeptide having SEQ ID No.: 2, and sequences substantially identical thereto. The method includes introducing a nucleic acid encoding the polypeptide into a host cell, wherein the nucleic acid is operably linked to a promoter, and culturing the host cell under conditions that allow expression of the nucleic acid, thereby producing the polypeptide.

Another aspect of the invention is a method of generating a variant including obtaining a nucleic acid having a sequence as set forth in SEQ ID No.: 1 or sequences substantially identical thereto, sequences complementary to the sequences of SEQ ID No.: 1, fragments comprising at least 30 consecutive nucleotides of the foregoing sequences, and changing one or more nucleotides in the sequence to another nucleotide, deleting one or more nucleotides in the sequence, or adding one or more nucleotides to the sequence.

Another aspect of the invention is a computer readable medium having stored thereon a sequence as set forth in SEQ ID No.: 1 sequences, and sequences substantially identical thereto, or a polypeptide sequence as set forth in SEQ ID No.: 2 amino acid sequences, and sequences substantially identical thereto.

Another aspect of the invention is an assay for identifying fragments or variants of SEQ ID No.: 2 amino acid sequences, and sequences substantially identical thereto, which retain the enzymatic function of the polypeptides of SEQ ID No.: 2 amino acid sequences, and sequences substantially identical thereto. The assay includes contacting the polypeptide of SEQ ID No.: 2 amino acid sequences, sequences substantially identical thereto, or polypeptide fragment or variant with a substrate molecule under conditions which allow the polypeptide fragment or variant to function, and detecting either a decrease in the level of substrate or an increase in the level of the specific reaction product of the reaction between the polypeptide and substrate thereby identifying a fragment or variant of such sequences.

BRIEF DESCRIPTION OF THE DRAWINGS

The following drawings are illustrative of embodiments of the invention and are not meant to limit the scope of the invention as encompassed by the claims.

FIG. 4 is SEQ ID No.: 1, the deoxyribonucleic acid (DNA) sequence of the present invention.

EXAMPLES

Example 1

Figure 1:
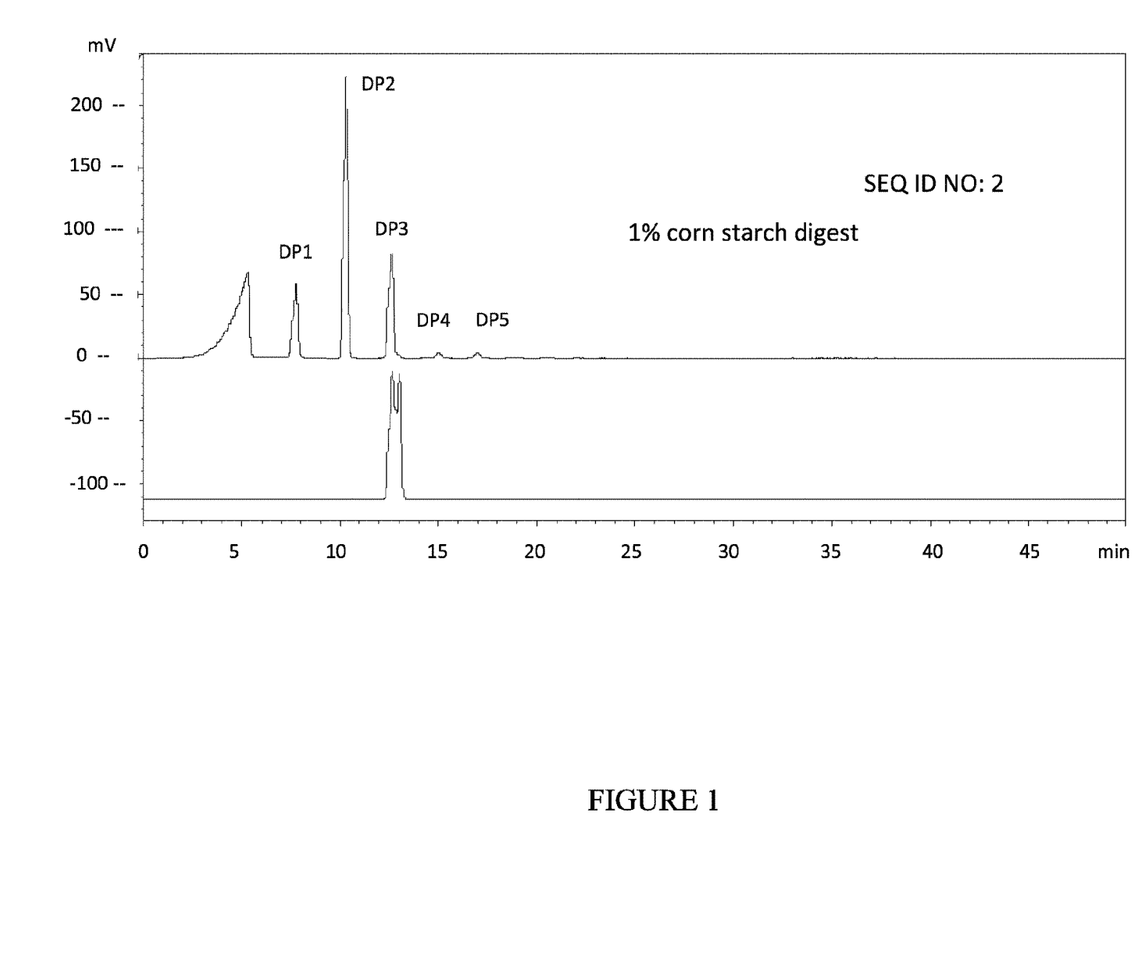
FIG. 1 is a chromatogram displaying the results of a digestion using the pullulanase of SEQ ID No.: 1 & 2 with a 1% corn starch substrate at 50 degrees Celcius, and as further described in Example 1.
Figure 2:
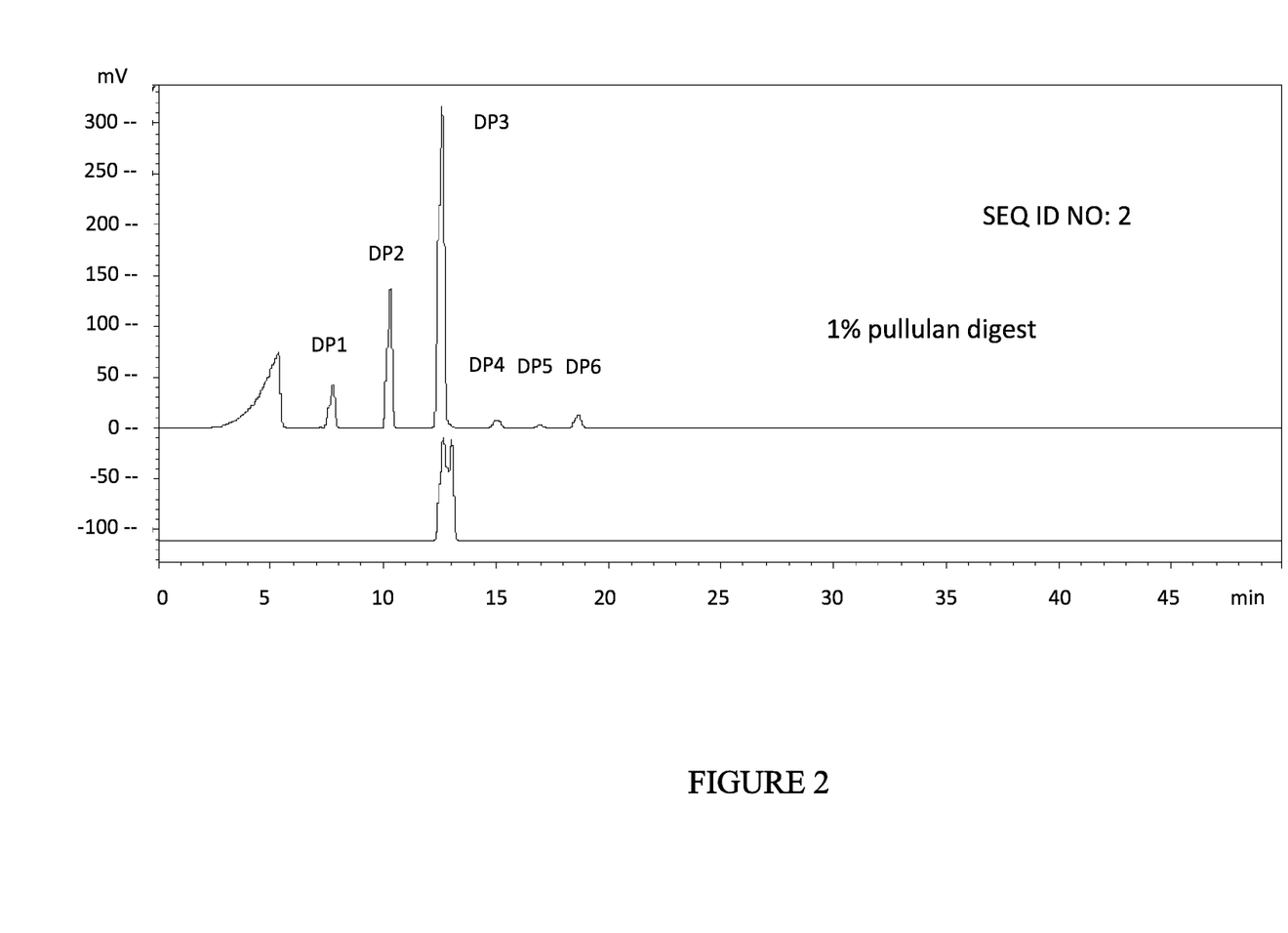
FIG. 2 is a chromatogram displaying the results of a digestion using the pullulanase of SEQ ID No.: 1 & 2 with a 1% pullulan at 50 degrees Celcius, and as further described in Example 1.
Figure 3:
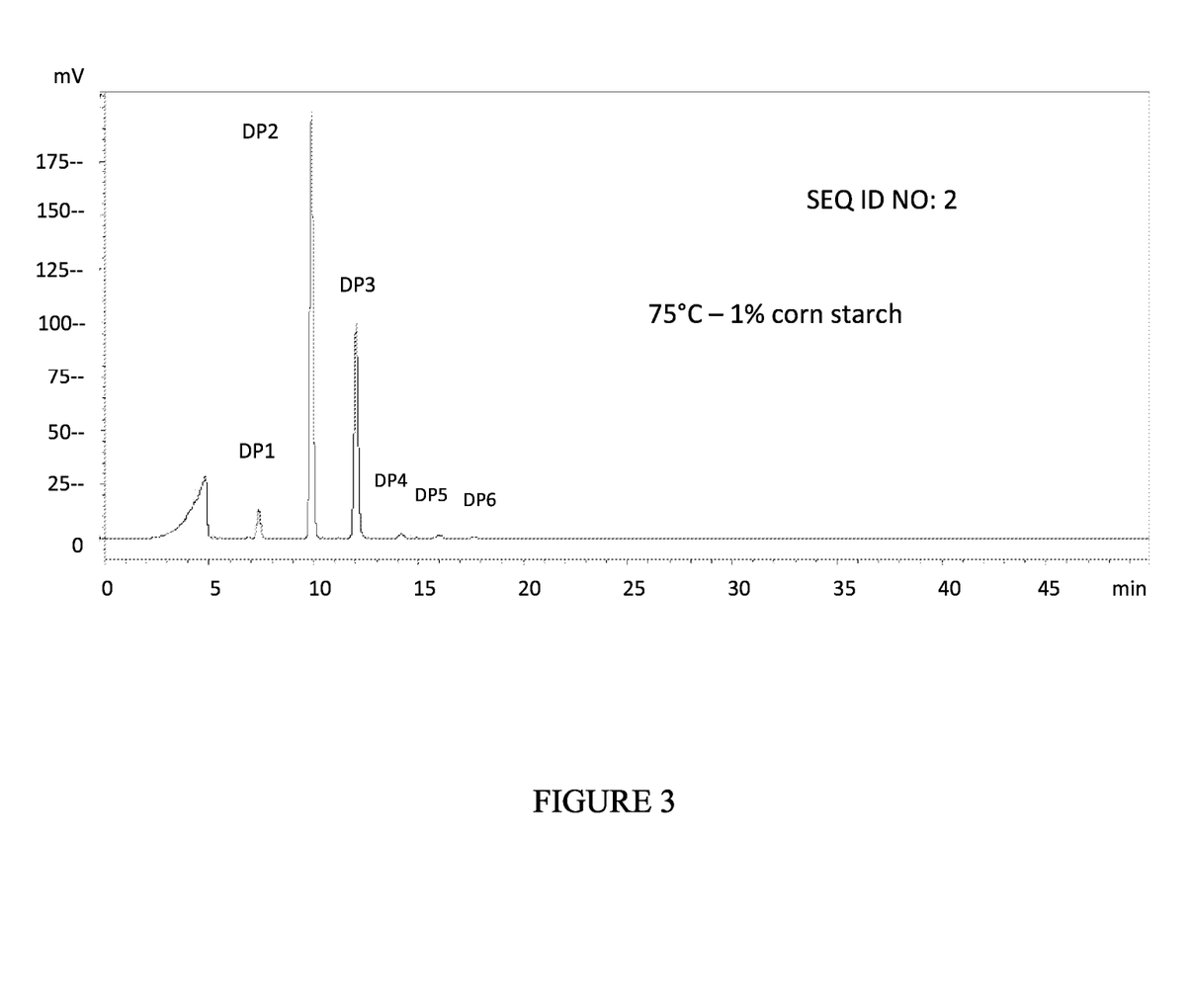
FIG. 3 is a chromatogram displaying the results of a digestion using the pullulanase of SEQ ID No.: 1 & 2 with a 1% corn starch substrate at 75 degrees Celcius, and as further described in Example 1.
Figure 5:
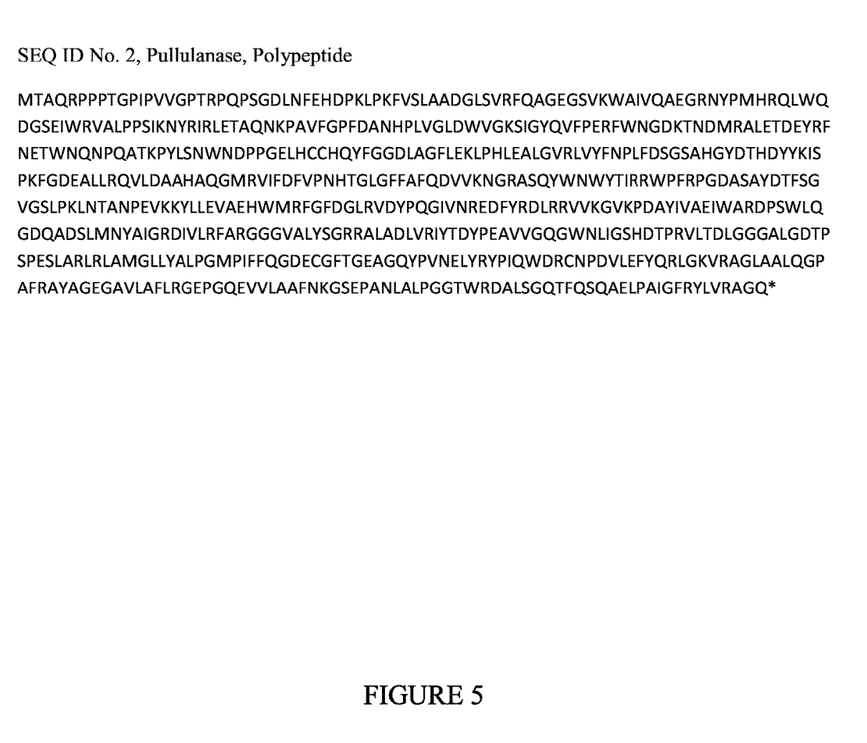
FIG. 5 is SEQ ID No.: 2, the amino acid sequence of the present invention.

The pullulanase of the present invention (as embodied by SEQ ID No.: 1 & 2) was tested against 1% solids using an aliquot from a trial cell lysate. The results shown in FIGS. 1, 2, and 3, show that the pullulanase of the present invention is able to cleave both alpha-1,6 and alpha-1,4 bonds. As displayed in FIG. 2, the pullulanase of the present invention (as embodied by SEQ ID No. 1 & 2) was assayed with 1% pullulan at 50 degrees Celsius. As displayed in FIG. 1, the pullulanase of the present invention (as embodied by SEQ ID NO 1 & 2) was assayed with 1% corn starch at 50 degrees Celcius. As displayed in FIG. 3, the pullulanase of the present invention (as embodied by SEQ ID No. 1 & 2) was assayed with 1% corn starch at 75 degrees Celsius. As indicated in FIGS. 1, 2, and 3, the enzyme is a type II pullulanase, as the reaction products (major peaks) are glucose, maltose, and maltotriose. Additionally, the peak 2 product was confirmed to be maltose and not isomaltose, while the peak 3 product was confirmed to be maltotriose and not panose.

Example 2

The pullulanase of the present invention (as embodied by SEQ ID No. 1 & 2) melting point or thermal denaturation was determined using differential scanning calorimetry. The Tm of the present invention (as embodied by SEQ ID No. 1 & 2) is 84 degrees Celsius.

DETAILED DESCRIPTION

The present invention relates to a pullulanase enzyme, polynucleotides encoding the enzymes, methods of making and using these polynucleotides and polypeptides. The invention is directed to novel polypeptides having pullulanase activity, nucleic acids encoding them. The polypeptides of the invention can be used in a variety of commercial, medical, and industrial contexts. The polypeptides of the invention can be used as, e.g., an additive for a detergent, for processing foods and for chemical synthesis utilizing a reverse reaction, saccharification of starch, liquefaction of starch, production of high-maltose corn syrup, production of high-fructose corn syrup, starch processing, ethanol production, production of cyclodextrins, and production of low-calorie beer, in the baking industry, as well as dental plaque control.

In one aspect of the invention the pullulanase is a type II pullulanase or is capable of cleaving both alpha-1,6 and alpha-1,4 bonds. In another aspect of the invention the pullulanase of the present invention is capable of cleaving both alpha-1,6 and alpha-1,4 of pullulan yielding glucose, maltose, and maltotriose. In a further embodiment of the present invention the pullulanase of the present invention is thermostable and or thermotolerant. In a further embodiment of the invention the pullulanase of the present invention is active at 75 degrees Celsius. In a further embodiment of the invention, the pullulanase of the invention is capable of saccharification of starch at higher temperatures then currently employed, thereby reducing processing times, and increasing yields due to lessening the rate of retrogradation of materials resulting in drops in temperature. In a further embodiment of the present invention the pullulanase is capable of enhancing ethanol or glucose production by digesting limit dextrans that an amylase cannot digest.

In a further embodiment of the present invention the pullulanase of the present invention is coupled with an amylase enzyme.

In one aspect, the nucleic acid encodes at least one polypeptide having pullulanase activity.

"Synthetic" nucleic acids (including oligonucleotides), polypeptides or proteins of the invention include those prepared by any chemical synthesis, e.g., as described, below.

The phrases "nucleic acid" or "nucleic acid sequence" includes oligonucleotides, nucleotides, polynucleotides, or to a fragment of any of these, to DNA or RNA (e.g., mRNA, rRNA, tRNA) of genomic, recombinant or synthetic origin which may be single-stranded or double-stranded and may represent a sense or antisense strand, to peptide nucleic acid (PNA), or to any DNA-like or RNA-like material, natural or synthetic in origin, including, e.g., iRNA such as miRNA or siRNA, ribonucleoproteins (e.g., iRNPs). The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156.

"Recombinant" polypeptides or proteins refer to polypeptides or proteins produced by recombinant DNA techniques; e.g., produced from cells transformed by an exogenous DNA construct encoding the desired polypeptide or protein. The term "gene" includes a nucleic acid sequence comprising a segment of DNA involved in producing a transcription product (e.g., a message), which in turn is translated to produce a polypeptide chain, or regulates gene transcription, reproduction or stability. Genes can include regions preceding and following the coding region, such as leader and trailer, promoters and enhancers, as well as, where applicable, intervening sequences (introns) between individual coding segments (exons).

The invention provides isolated and recombinant nucleic acids, including expression cassettes such as expression vectors encoding the polypeptides of the invention. The invention provides probes comprising or consisting of nucleic acids of the invention. The invention also includes methods for discovering new pullulanase sequences using the nucleic acids of the invention. The invention also includes methods for inhibiting the expression of pullulanase genes, transcripts and polypeptides using the nucleic acids of the invention.

The nucleic acids of the invention can be made, isolated and/or manipulated by, e.g., cloning and expression of cDNA libraries, amplification of message or genomic DNA by PCR, and the like. In practicing the methods of the invention, homologous genes can be modified by manipulating a template nucleic acid, as described herein. The invention can be practiced in conjunction with any method or protocol or device known in the art, which are well described in the scientific and patent literature.

What is claimed is:

1. A method of hydrolyzing a starch linkage comprising:
contacting a substance containing the starch with an isolated, synthetic, or recombinant polypeptide having pullulanase activity comprising
(a) an amino acid sequence having the sequence according to SEQ ID No. 2;
(b) an amino acid sequence encoded by the nucleic acid sequence having the sequence according to SEQ ID NO: 1; or
(c) the amino acid sequence of (a) or (b), and consisting at least one conservative amino acid residue substitution; and
recovering the hydrolyzed starch containing substance.

2. A method of hydrolyzing a starch linkage comprising:
contacting a substance containing the starch with an isolated, synthetic, or recombinant polypeptide having pullulanase activity comprising
(a) an amino acid sequence having the sequence according to SEQ ID No. 2;
(b) an amino acid sequence encoded by the nucleic acid sequence having the sequence according to SEQ ID NO: 1; or
(c) the amino acid sequence of (a) or (b), and consisting at least one conservative amino acid residue substitution; and
further comprising addition of further pullulanase, or a combination thereof.

3. A method for liquefying a starch containing composition comprising:
contacting the starch containing composition with an isolated, synthetic, or recombinant polypeptide having pullulanase activity comprising
(a) an amino acid sequence having the sequence according to SEQ ID No. 2;
(b) an amino acid sequence encoded by the nucleic acid sequence having the sequence according to SEQ ID NO: 1; or
(c) the amino acid sequence of (a) or (b), and consisting at least one conservative amino acid residue substitution; and
recovering the liquefied starch containing composition.

4. A method for liquefying a starch containing composition comprising:
contacting the starch containing composition with an isolated, synthetic, or recombinant polypeptide having pullulanase activity comprising
(a) an amino acid sequence having the sequence according to SEQ ID No. 2;
(b) an amino acid sequence encoded by the nucleic acid sequence having the sequence according to SEQ ID NO: 1; or
(c) the amino acid sequence of (a) or (b), and consisting at least one conservative amino acid residue substitution; and further comprising addition of further pullulanase, or a combination thereof.

5. A method for starch liquefaction comprising:
contacting said starch with an isolated, synthetic, or recombinant polypeptide having pullulanase activity under conditions sufficient for said liquefaction, wherein the polypeptide comprises
(a) an amino acid sequence having the sequence according to SEQ ID No. 2;
(b) an amino acid sequence encoded by the nucleic acid sequence having the sequence according to SEQ ID NO: 1; or
(c) the amino acid sequence of (a) or (b), and consisting at least one conservative amino acid residue substitution; and
recovering the liquefied starch.

6. A method for starch liquefaction comprising:
contacting said starch with an isolated, synthetic, or recombinant polypeptide having pullulanase activity under conditions sufficient for said liquefaction, wherein the polypeptide comprises
(a) an amino acid sequence having the sequence according to SEQ ID No. 2;
(b) an amino acid sequence encoded by the nucleic acid sequence having the sequence according to SEQ ID NO: 1; or
(c) the amino acid sequence of (a) or (b), and consisting at least one conservative amino acid residue substitution;
further comprising addition of further pullulanase, or a combination thereof.

7. A method for producing a high-maltose or a high-glucose syrup or a mixed syrup comprising:
contacting a starch containing substance with an isolated, synthetic, or recombinant polypeptide with pullulanase activity having
(a) an amino acid sequence having the sequence according to SEQ ID No. 2;
(b) an amino acid sequence encoded by the nucleic acid sequence having the sequence according to SEQ ID NO: 1; or
(c) the amino acid sequence of (a) or (b), and consisting at least one conservative amino acid residue substitution; and
recovering the high-maltose or the high glucose syrup or the mixed high syrup.

8. A method for producing a high-maltose or a high-glucose syrup or a mixed syrup comprising:
contacting a starch containing substance with an isolated, synthetic, or recombinant polypeptide with pullulanase activity having
(a) an amino acid sequence having the sequence according to SEQ ID No. 2;
(b) an amino acid sequence encoded by the nucleic acid sequence having the sequence according to SEQ ID NO: 1; or
(c) the amino acid sequence of (a) or (b), and consisting at least one conservative amino acid residue substitution; and
further comprising addition of further pullulanase, or a combination thereof.

9. The method of claim 1, wherein:
(a) the pullulanase activity is thermostable;
(b) the polypeptide retains an pullulanase activity under conditions comprising a temperature range of between about 37° C. to about 84° C.;
(c) the pullulanase activity is thermotolerant; or
(d) the polypeptide retains a pullulanase activity after exposure to a temperature in the range from greater than 37° C. to about 84° C.

10. The method of claim 3, wherein:
(a) the pullulanase activity is thermostable;
(b) the polypeptide retains an pullulanase activity under conditions comprising a temperature range of between about 37° C. to about 84° C.;
(c) the pullulanase activity is thermotolerant; or
(d) the polypeptide retains a pullulanase activity after exposure to a temperature in the range from greater than 37° C. to about 84° C.

11. The method of claim 5, wherein:
(a) the pullulanase activity is thermostable;
(b) the polypeptide retains an pullulanase activity under conditions comprising a temperature range of between about 37° C. to about 84° C.;
(c) the pullulanase activity is thermotolerant; or
(d) the polypeptide retains a pullulanase activity after exposure to a temperature in the range from greater than 37° C. to about 84° C.

12. The method of claim 1, further comprising addition of further pullulanase, or a combination thereof.

13. The method of claim 3, further comprising addition of further pullulanase, or a combination thereof.

14. The method of claim 5, further comprising addition of further pullulanase, or a combination thereof.

15. The method of claim 2, wherein:
(a) the pullulanase activity is thermostable;
(b) the polypeptide retains an pullulanase activity under conditions comprising a temperature range of between about 37° C. to about 84° C.;
(c) the pullulanase activity is thermotolerant; or
(d) the polypeptide retains a pullulanase activity after exposure to a temperature in the range from greater than 37° C. to about 84° C.

16. The method of claim 4, wherein:
(a) the pullulanase activity is thermostable;
(b) the polypeptide retains an pullulanase activity under conditions comprising a temperature range of between about 37° C. to about 84° C.;
(c) the pullulanase activity is thermotolerant; or
(d) the polypeptide retains a pullulanase activity after exposure to a temperature in the range from greater than 37° C. to about 84° C.

17. The method of claim 6, wherein:
(a) the pullulanase activity is thermostable;
(b) the polypeptide retains an pullulanase activity under conditions comprising a temperature range of between about 37° C. to about 84° C.;
(c) the pullulanase activity is thermotolerant; or
(d) the polypeptide retains a pullulanase activity after exposure to a temperature in the range from greater than 37° C. to about 84° C.

18. The method of claim 8, wherein:
(a) the pullulanase activity is thermostable;
(b) the polypeptide retains an pullulanase activity under conditions comprising a temperature range of between about 37° C. to about 84° C.;
(c) the pullulanase activity is thermotolerant; or
(d) the polypeptide retains a pullulanase activity after exposure to a temperature in the range from greater than 37° C. to about 84° C.

* * * * *